United States Patent
Yamayoshi (10) Patent No.: US 6,977,990 B2
(45) Date of Patent: Dec. 20, 2005

(54) IMAGE SENSING SYSTEM

(75) Inventor: Junichi Yamayoshi, West Newport Beach, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/642,232

(22) Filed: Aug. 18, 2003

(65) Prior Publication Data

US 2004/0071264 A1    Apr. 15, 2004

Related U.S. Application Data (62) Division of application No. 09/553,859, filed on Apr. 21, 2000, now Pat. No. 6,707,880.

(30) Foreign Application Priority Data

Apr. 27, 1999   (JP)   ................................. 11-119629

(51) Int. Cl.$^7$ ............................................. H05G 1/56

(52) U.S. Cl. ........................................ 378/115; 378/91

(58) Field of Search .............................. 378/62, 19, 4, 378/92, 98.8, 115–117, 210, 91; 250/370.08, 250/370.09, 208.1

(56) References Cited

U.S. PATENT DOCUMENTS

| | | | |
|---|---|---|---|
| 4,146,794 A | | 3/1979 | Duinker .................. 250/445 T |
| 5,001,735 A | * | 3/1991 | Sammon ...................... 378/96 |
| 5,084,911 A | | 1/1992 | Sezan et al. .................. 378/96 |
| 5,313,241 A | * | 5/1994 | Seim .......................... 396/578 |
| 5,361,215 A | * | 11/1994 | Tompkins et al. .......... 700/300 |
| 5,473,659 A | | 12/1995 | Haendle et al. ............ 378/98.2 |
| 5,867,561 A | | 2/1999 | Strasser et al. ............ 378/98.2 |
| 6,707,880 B2 | * | 3/2004 | Yamayoshi .................. 378/92 |

FOREIGN PATENT DOCUMENTS

| | | | | |
|---|---|---|---|---|
| GB | 890234 | | 2/1962 | |
| GB | 2003010 | | 2/1979 | ............ H05G 1/58 |
| GB | 2003010 A | * | 2/1979 | |

\* cited by examiner

*Primary Examiner*—David V. Bruce
*Assistant Examiner*—Hoon Song
(74) *Attorney, Agent, or Firm*—Fitzpatrick, Cella, Harper & Scinto

(57) ABSTRACT

This invention is to provide a system which has a plurality of sensor units and can efficiently sense an image. A sensing system includes a plurality of sensor units, a plurality of selection switches that are arranged in correspondence with the plurality of sensor units, respectively, and select corresponding sensor units, and a control circuit for setting a sensor unit selected by the selection switch in a ready state and an unselected sensor unit in a sleep state.

4 Claims, 7 Drawing Sheets

IMAGE SENSING SYSTEM

CROSS-REFERENCE TO RELATED APPLICATION

This application is a division of application Ser. No. 09/553,859, filed Apr. 21, 2000, now U.S Pat. No. 6,707, 880.

BACKGROUND OF THE INVENTION

1. Field of the Invention

The present invention relates to a sensing system using a plurality of sensor units, and a sensor unit used in the sensing system.

2. Related Background Art

X-ray sensing aiming at medical diagnosis is often done using a film screen system which combines intensifying screen and an X-ray radiographic film. According to this method, X-rays transmitted through an object contain the internal information of the object. This information is converted into visible light proportional to the intensity of the X-rays by the intensifying screen. The X-ray radiographic film is exposed to the light, and an X-ray image is formed on the film.

Recently, digital X-ray image sensing apparatuses are becoming popular in which X-rays are converted into visible light proportional to the intensity of the X-rays by a phosphor, the light is converted into an electrical signal using a photoelectric conversion element, and the signal is converted into digital data by an A/D conversion circuit.

In a sensing room for general X-ray image sensing, normally, an upright stand for a thoracic portion and a table for an abdominal portion or a leg are prepared to cope with all target sensing portions, using a cassette together. After sensed on the upright stand, the patient moves to the table for the next required sensing. At this time, the X-ray technician supports and positions the patient to prepare for appropriate sensing. After positioning, the X-ray technician goes back to the operation room to radiate X-rays. When a film screen system is used, the patient must wait after sensing until film development is ended. After confirming upon development that normal sensing has been performed, the next sensing operation starts. To the contrary, when a digital X-ray sensing apparatus is used, the X-ray technician positions the patient and then returns to the operation room to radiate X-rays. The resultant X-ray image can be confirmed on the display monitor in several seconds. Hence, the X-ray technician can immediately start the next sensing.

Figure 1:
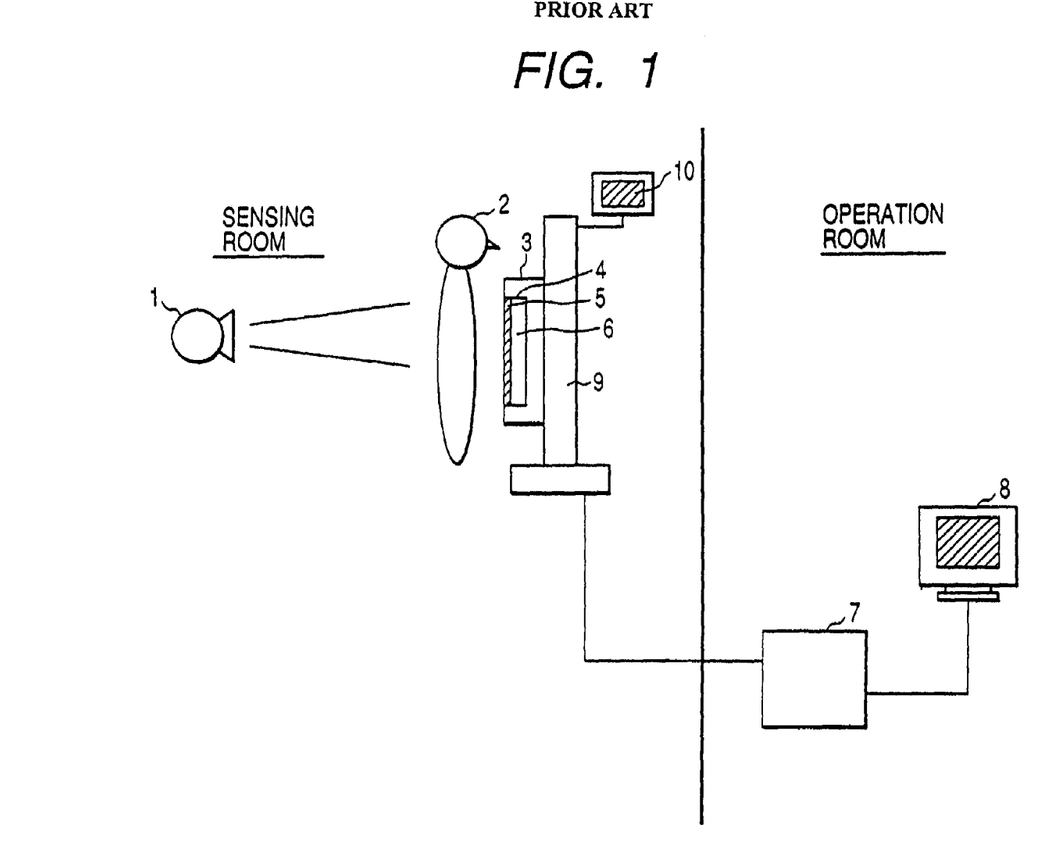
FIG. 1 is a view showing a prior art.

FIG. 1 shows a conventional scheme of general sensing using a digital X-ray sensing apparatus. An upright stand 9 having a sensor unit 3 is prepared in a sensing room and connected to a control section 7 in an operation room. An X-ray technician appropriately positions a patient 2 in front of the upright stand 9 first. The X-ray technician returns to the operation room and presses an X-ray radiation switch. X-rays are radiated from an X-ray generation apparatus 1 and transmitted through the patient 2. The X-rays with the internal information of the patient 2 become incident on the sensor unit 3. A solid-state image sensing apparatus 4 in the sensor unit 3 is constructed by bonding a phosphor 5 for converting X-rays into visible light proportional to the intensity of the X-rays to a photoelectric conversion apparatus 6 for converting the visible light into an electrical signal proportional to the light intensity. The X-ray image data converted into an electrical signal by the photoelectric conversion apparatus 6 is A/D-converted, transferred to the control section 7 as digital data, and displayed on display sections 8 and 10. Since several seconds are normally required from X-ray radiation to image display, the X-ray technician enters the sensing room to attend the patient 2 immediately after X-ray radiation and confirms the image on the display section 10.

In this prior art, since the apparatus has only the thoracic sensor unit, only the information of the thoracic portion of the patient is obtained. To obtain information except the thoracic information, e.g., abdominal information, an abdominal sensor unit must be prepared in the sensing room independently of the thoracic sensor unit.

When the apparatus has the thoracic and abdominal sensor units, the information of the thoracic portion of the patient is obtained first. Then, the patient moves to the abdominal sensor unit to obtain abdominal information.

At this time, the abdominal sensor unit must transit from the sleep state (low current state) in the nonuse mode to the ready state (normal current state). Normally, the photoelectric conversion apparatus 6 in the sensor unit requires several seconds for the transit period in which the ready state is set. For this reason, the next sensing cannot be started during this time. When the thoracic sensor unit and abdominal sensor unit are simultaneously set in the ready state, the problem of wait time can be avoided. However, the service life of the solid-state image sensing apparatus normally becomes short in inverse proportion to the ready-state time.

SUMMARY OF THE INVENTION

It is an object of the present invention to switch, in a sensing system having a plurality of sensor units, between the sleep state (or power-OFF state) and the ready state (or a power-ON state) of each sensor unit at an effective timing.

In order to achieve the above object, according to aspect of the present invention, there is provided a sensing system comprising a plurality of sensor units, a plurality of selection means arranged in correspondence with the plurality of sensor units respectively, for selecting the corresponding sensor units, and control means for setting a sensor unit selected by the selection means in a ready state and an unselected sensor unit in a sleep state.

According to another aspect of the present invention, there is also provided a sensing system comprising a plurality of sensor units, a plurality of selection means arranged in correspondence with the plurality of sensor units respectively, for selecting the corresponding sensor units, and control means for powering on a sensor unit selected by the selection means and powering off an unselected sensor unit.

Other objects, features, and advantages of the present invention will be apparent from the following description taken in conjunction with the accompanying drawings.

DESCRIPTION OF THE PREFERRED EMBODIMENTS

The first embodiment of the present invention will be described with reference to FIGS. 2 and 3.

Figure 2:
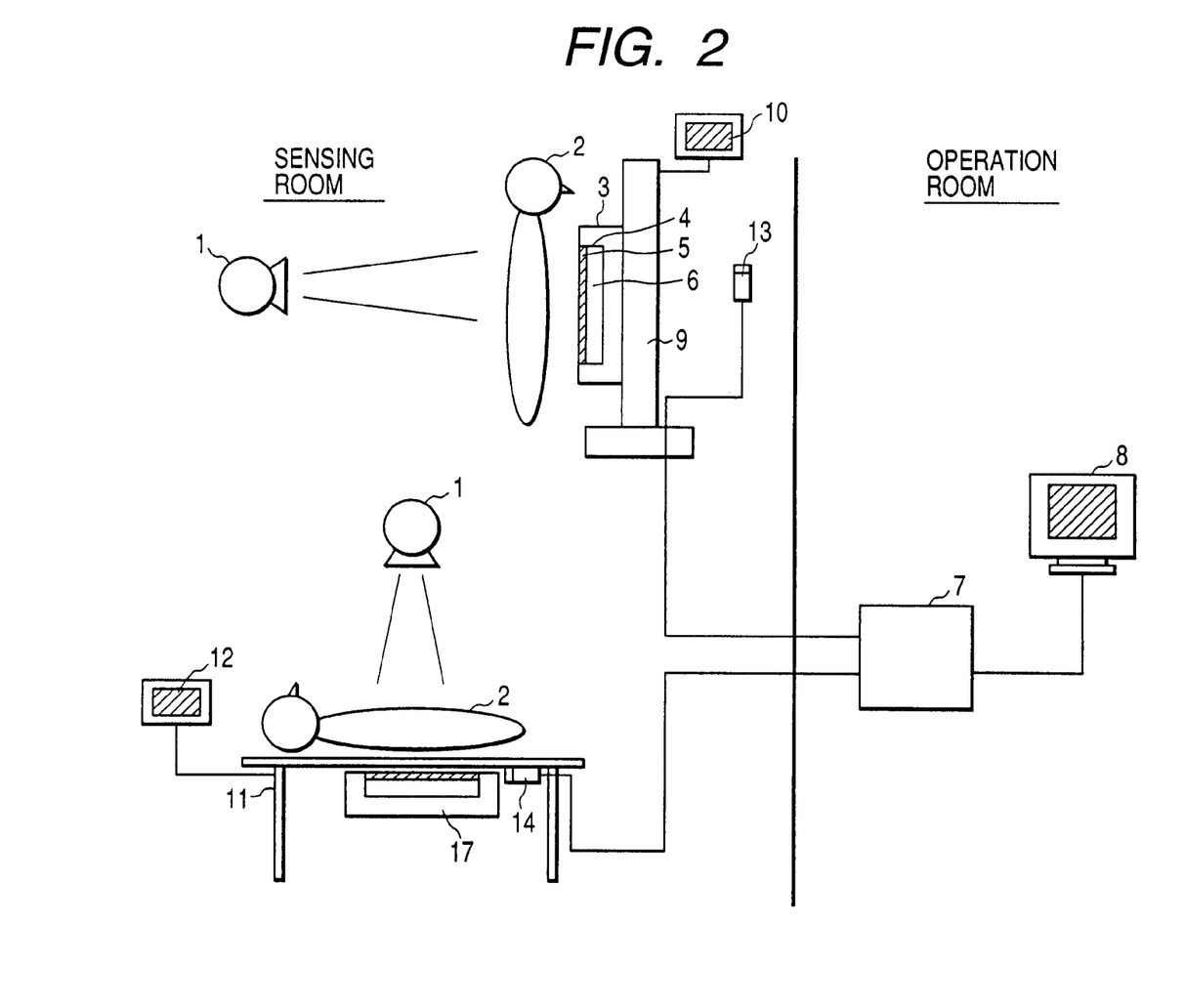
FIG. 2 is a view showing the first embodiment of the present invention.
Figure 3:
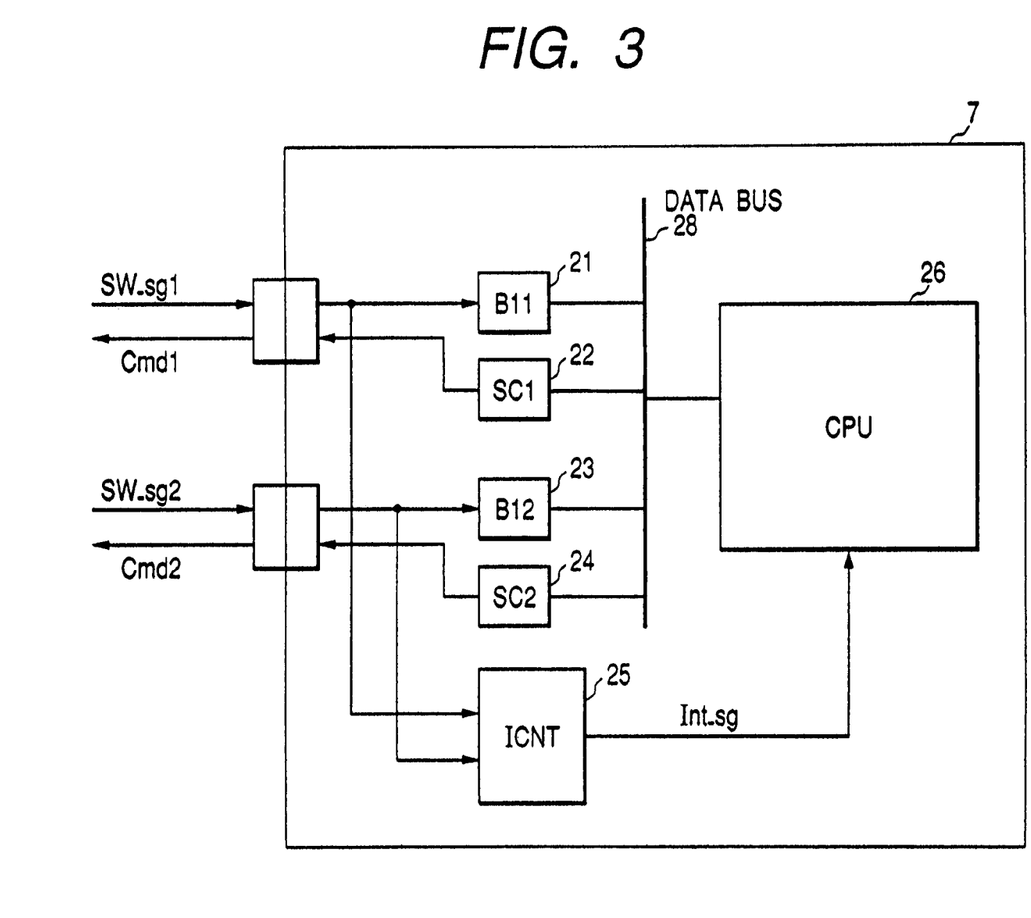
FIG. 3 is a view showing the first embodiment of the present invention.

FIG. 2 is a view for explaining a sensing system. FIG. 3 is a view showing details of the control section of the sensing system shown in FIG. 2. Referring to FIG. 2, an upright stand 9 and table 11 each having a sensor unit are prepared in a sensing room and connected to a control section 7 in an operation room. A patient 2 stands first in front of the upright stand 9 and is appropriately positioned. An X-ray technician returns to the operation room and presses an X-ray radiation switch. X-rays are radiated from an X-ray generation apparatus 1 and transmitted through the patient 2. The X-rays having internal information of the patient 2 become incident on the sensor unit 3. The sensor unit 3 includes a solid-state image sensing apparatus constructed by bonding a phosphor 5 for converting X-rays into visible light proportional to the intensity of the X-rays to a photoelectric conversion apparatus 6 for converting the visible light into an electrical signal proportional to the light intensity. The photoelectric conversion apparatus requires several seconds for the transit period in which the apparatus shifts from the sleep state (low current state) in the nonuse mode to the ready state (normal current state). The X-ray image data converted into an electrical signal by the photoelectric conversion apparatus 6 is A/D-converted, transferred to the control section 7 as digital data, and displayed on display section 8 in the operation room and display section 10 in the sensing room. Since several seconds are normally required from X-ray radiation to image display, the X-ray technician enters the sensing room to attend the patient 2 immediately after X-ray radiation and confirms the image on the display section 10. If the X-ray image is normal, the X-ray technician presses a switch 14 as a selection means attached to the side surface portion of the sensing table 11. The X-ray technician positions the patient 2 to prepare for sensing on the table 11. The state of the switch 14 is monitored by the control section 7. When the switch 14 is pressed, the upright stand 9 is set in the sleep state, and the sensing table 11 is shifted to the ready state. Each of the switches 13 and 14 has a lamp indicating the state of the sensor. The lamp of the switch 13 is OFF. The lamp of the switch 14 blinks when the sensor is transiting to the ready state, and is turned on in the ready state. A transit time of several seconds is required until the ready state is set, as described above. However, the ready state is set while the patient is being positioned. The X-ray technician returns to the operation room and immediately switches the X-ray radiation switch to sense an image.

The control section 7 shown in FIG. 2 will be described next in detail with reference to FIG. 3. In the control section 7, a signal SW_sg1 from the switch 13 can be simultaneously input to an input buffer B11 21 connected to a data bus 28 of a CPU 26, and an interrupt controller ICNT 25. A signal SW_sg2 from the switch 14 can also be simultaneously input to an input buffer B12 23 connected to the data bus 28 of the CPU 26, and the interrupt controller ICNT 25. The interrupt controller ICNT 25 monitors these signals and, when one of the signals is enabled, generates an interrupt signal INT_sg to the CPU 26. The CPU 26 reads the input buffer B11 21 and input buffer B12 23 on the data bus, thereby determining the pressed switch. In this example, since the switch 14 is pressed, the CPU 26 detects the signal SW_sg2. A command for setting the sleep state is transmitted from a serial IF controller SC1 22 connected to the data bus 28 to the sensor unit 3 through a command line Cmd1. In addition, a command for setting the ready state is transmitted from a serial IF controller SC2 24 to a sensor unit 17 through a command line Cmd2.

In this embodiment, two sensor units are used. However, three or more sensor units may be used.

The switch 14 is located on the side surface of the table 11. However, the switch 14 can be located at an optimum portion in accordance with the sensing operation of the X-ray technician who uses this switch.

In the above embodiment, a sensor unit in the nonuse mode is set in the sleep state, and that in the use mode is set in the ready state. However, a sensor unit in the nonuse mode may be set in a power-OFF state, and that in the use mode may be set in a power-ON state.

The second embodiment of the present invention will be described with reference to FIGS. 4, 5, and 6.

Figure 4:
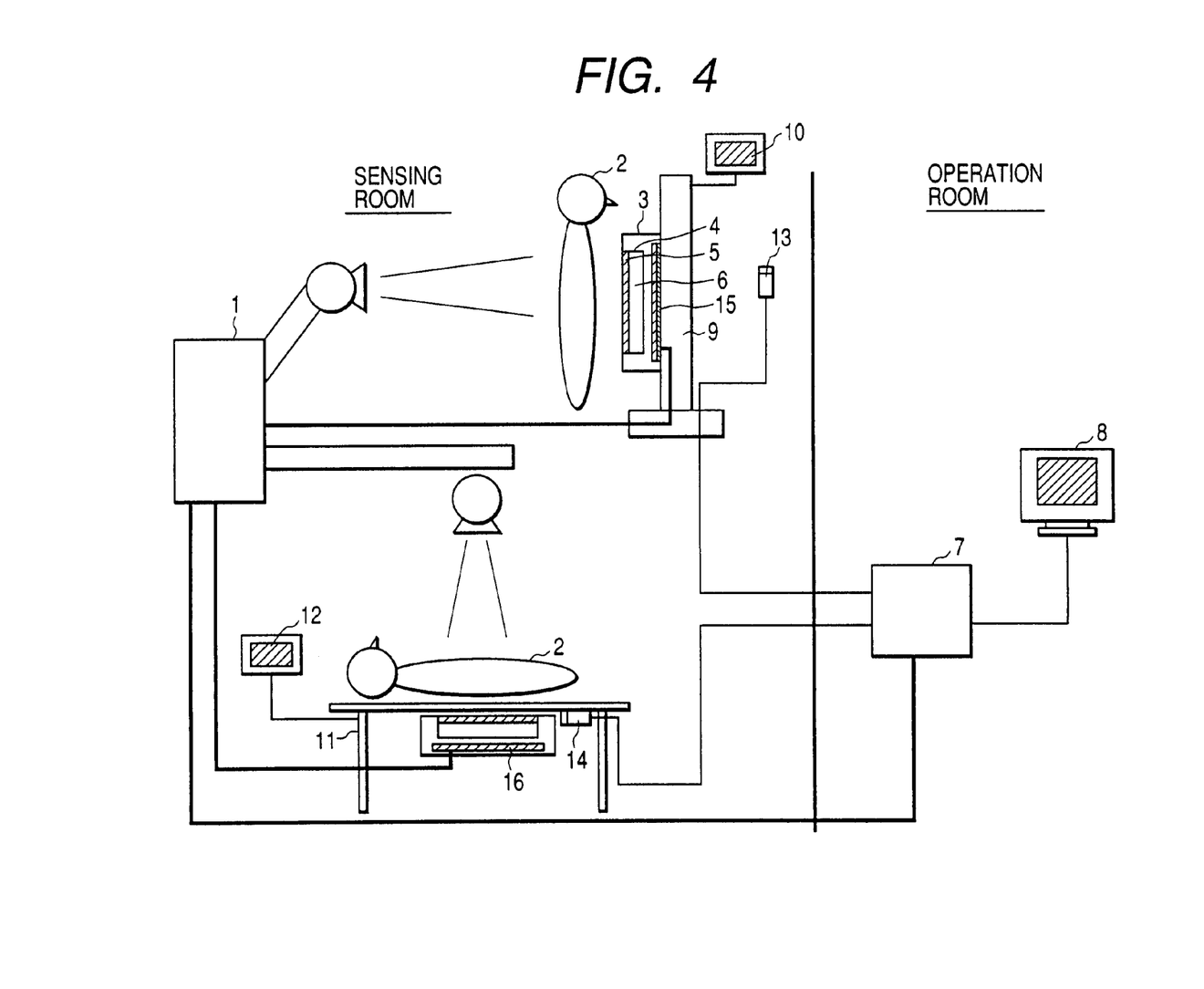
FIG. 4 is a view showing the second embodiment of the present invention.

FIG. 4 is a view for explaining a sensing system. FIG. 5 is a view showing details of the X-ray generation apparatus of the sensing system. FIG. 6 is a view showing details of the control section of the sensing system.

The operation of the second embodiment is the same as that of the first embodiment except that sensor units incorporate phototimers 15 and 16, respectively, and the sensing time can be controlled in accordance with the X-ray dose.

In general X-ray sensing, an image is normally sensed using an AEC (Auto Exposure Control) function of automatically adjusting the X-ray dose. AEC is also called a phototimer. In the phototimer, a phosphor is mounted on an element having a photoelectric effect and made to generate charges proportional to X-rays. When the charges reach a predetermined amount or more, a signal for cutting off the X-rays is output to the X-ray generation apparatus. As an element having a photoelectric effect, a semiconductor element such as a photodiode can be used. There is also a device which extracts visible light from a phosphor by a fiber and amplifies the light using a photomultiplier. The phototimers are connected to an X-ray generation apparatus 1, which is connected to a control section 7 such that they can communicate with each other. The control section 7 transfers a command to the X-ray generation apparatus 1 to switch between the phototimers 15 and 16 simultaneously with switching the sensor unit. The control section of this embodiment has a serial IF controller SC3 27 connected to a data bus 28, unlike the control section of the first embodiment, to transmit a command for switching between the phototimers 15 and 16 to a command line Cmd_X, as shown in FIG. 6. The X-ray generation apparatus 1 controls the X-ray generation timing in accordance with the output from the selected phototimer.

Figure 5:
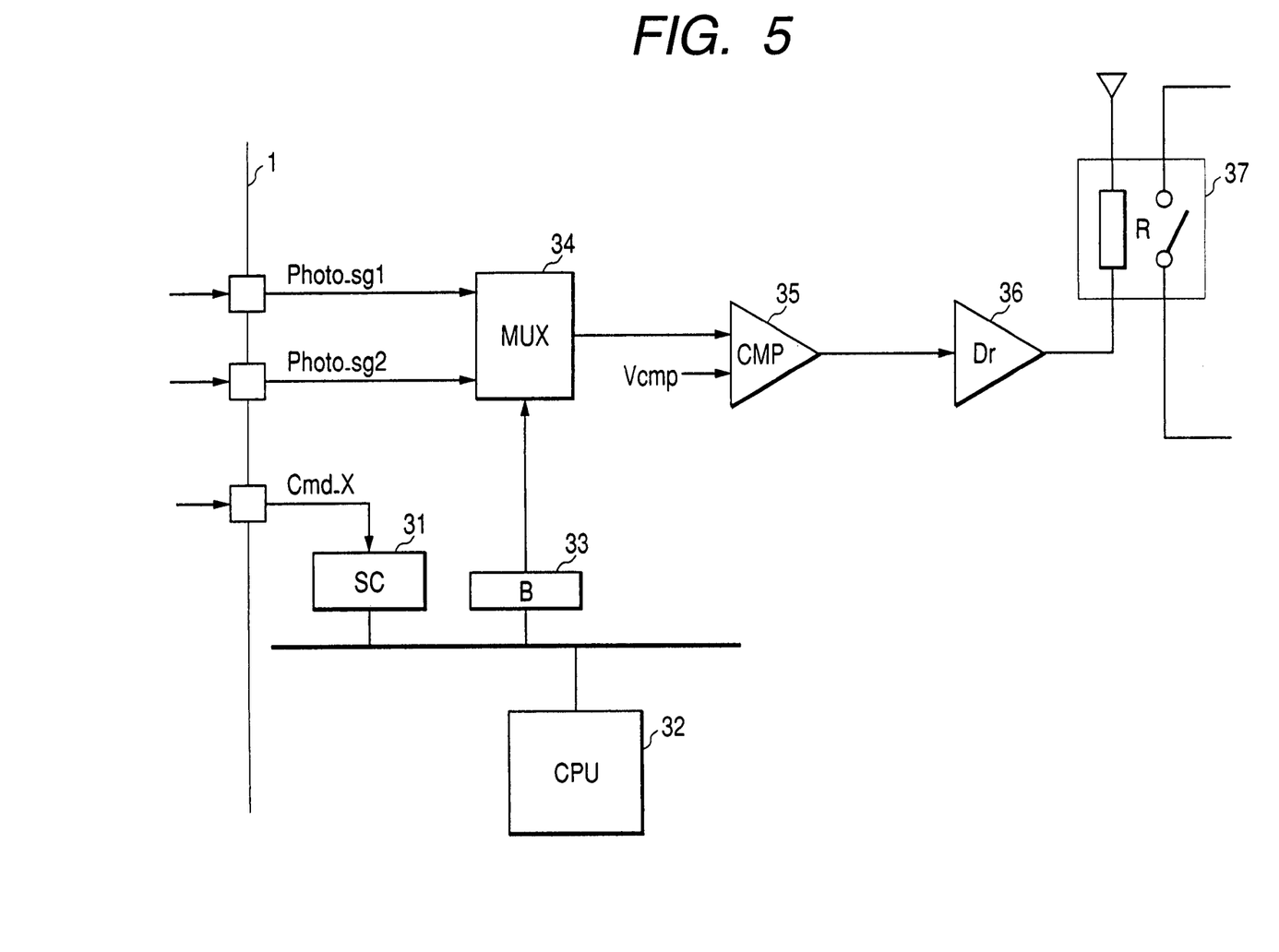
FIG. 5 is a view showing the second embodiment of the present invention.
Figure 6:
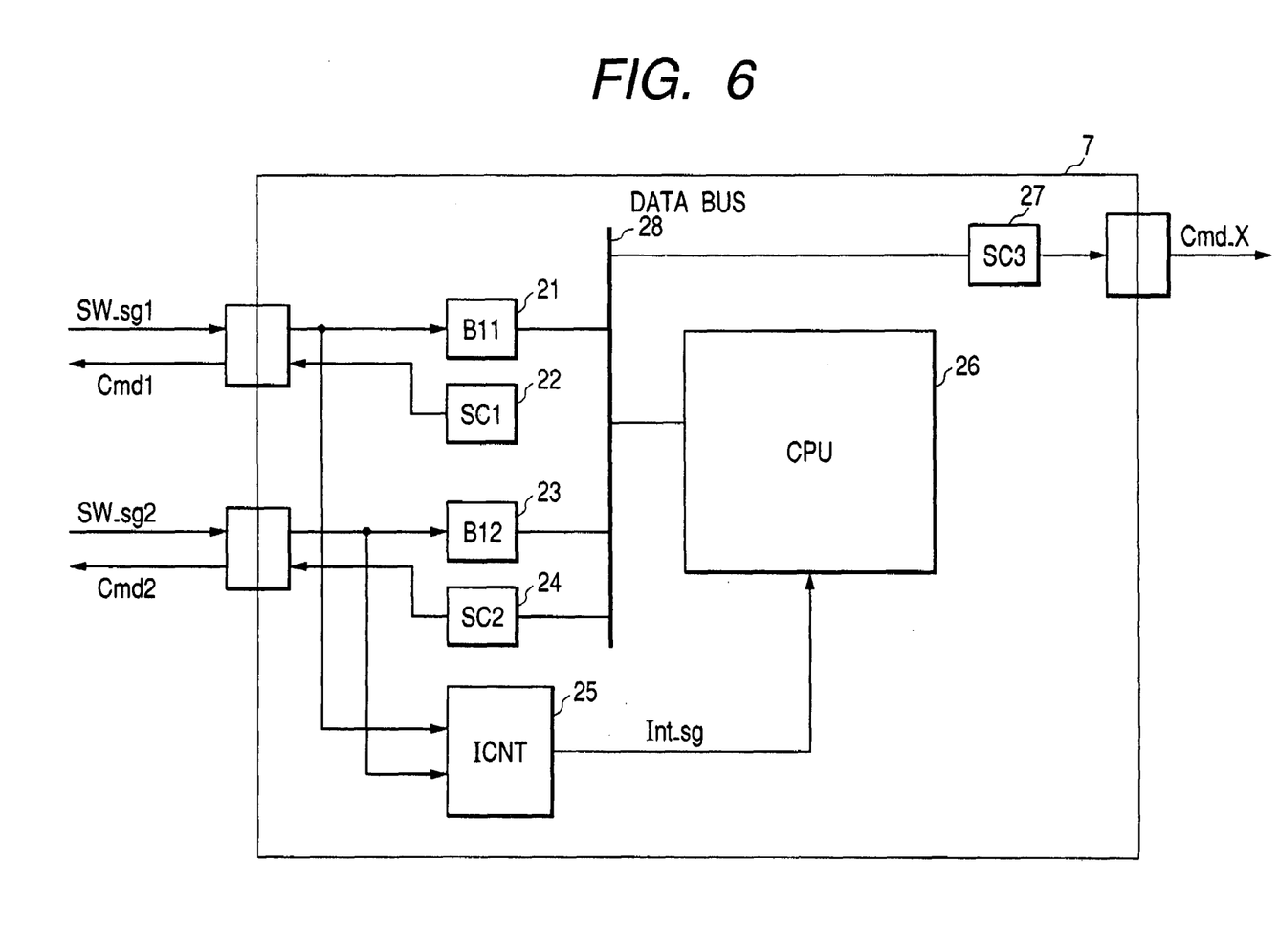
FIG. 6 is a view showing the second embodiment of the present invention.

As shown in FIG. 5, the X-ray generation apparatus 1 receives the switching request command for the phototimer 15 through the command line Cmd_X from the control section 7. A CPU 32 receives the command through a serial IF controller SC 31 and switches a multiplexer MUX 34 in accordance with the output signal from an output register B 33, thereby switching the signal of the phototimer from Photo_s1 to Photo_sg2. The output from the multiplexer MUX 34 is compared with a predetermined voltage Vcmp by a comparator CMP 35. When the output from the multiplexer MUX 34 is equal to or larger than the voltage Vcmp, a relay driving circuit Dr 36 disconnects a relay R 37 for ON/OFF-controlling X-ray generation.

Figure 7:
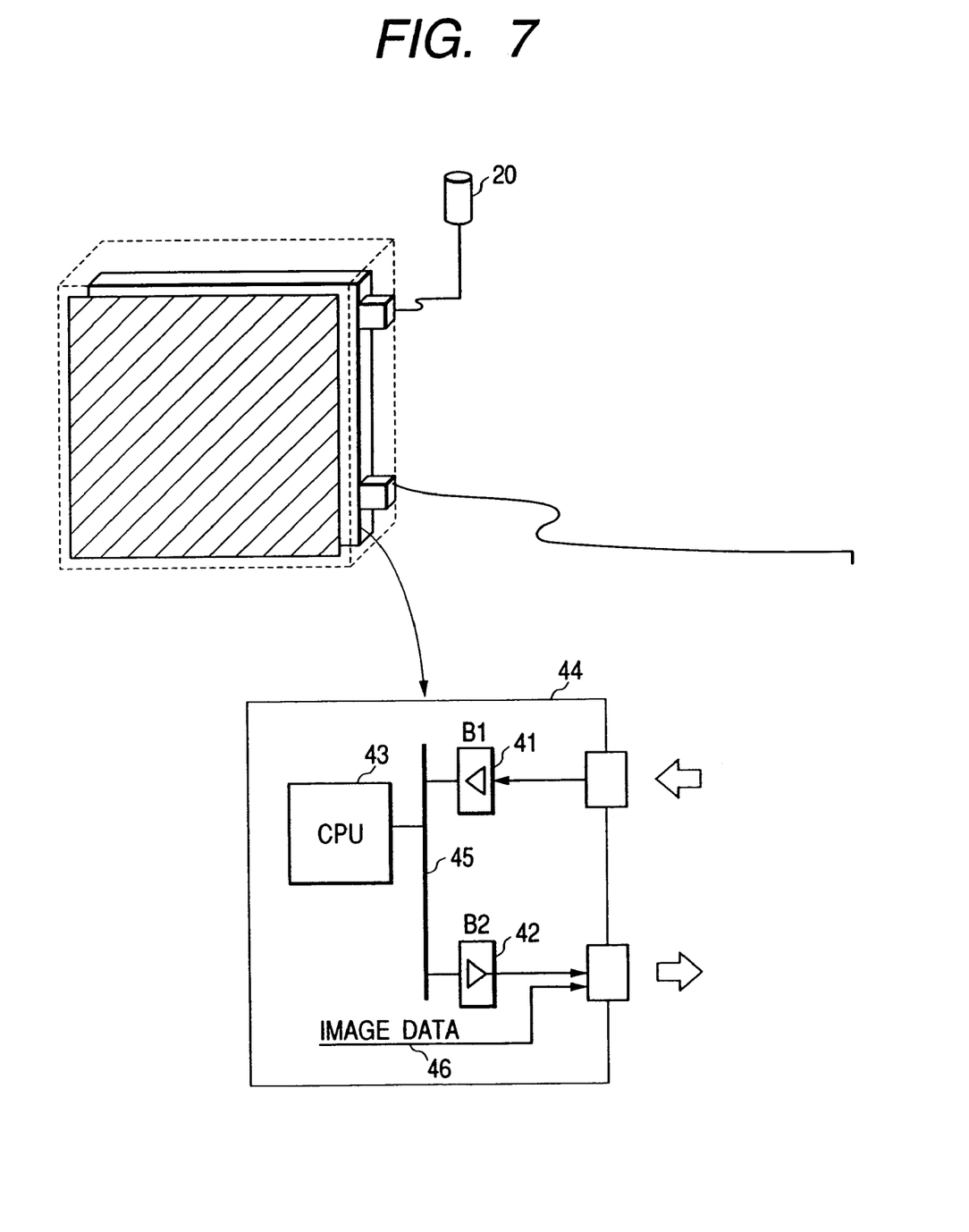
FIG. 7 is a view showing the third embodiment of the present invention.

The third embodiment of the present invention will be described with reference to FIG. 7.

In this embodiment, each of sensor unit changeover switches 13 and 14 described in the first and second embodiments is connected to a control circuit 44 belonging to the photoelectric conversion apparatus in the sensor unit. As shown in FIG. 7, the line of a switch 20 is connected to an input register B1 41 connected to the data bus of a CPU 43, so the CPU 43 can monitor the state of the switch 20. When the switch 20 is pressed, and the CPU 43 detects it, the CPU 43 writes a signal representing it in an output register B2 42 connected to a data bus 45. The output from the output register B2 42 is connected to a control section 7 of the main body together with an image data line 46 for sending image data. The control section 7 is requested to switch the sensor unit having the pressed switch 20 to the ready state.

In the systems of the first to third embodiments, a child patient may accidentally press the switch 13, 14, or 20 in his or her reach. As a measure against this situation, switch enable and disable items of an X-ray sensor unit are provided in the user interface section of the control section 7, and the switch 13 or 14 is disabled as needed.

As has been described above, when a sensor unit selection means is prepared in correspondence with each sensor unit, for example, the X-ray technician can switch the sensor unit at an effective timing, and an efficient sensing sequence can be realized.

Many widely different embodiments of the present invention may be constructed without departing from the spirit and scope of the present invention. It should be understood that the present invention is not limited to the specific embodiments described in the specification, except as defined in the appended claims.

What is claimed is:

1. An image sensing system comprising:
   a plurality of sensor units, each of which is adapted for converting a radiation ray into an electrical signal;
   at least one selection unit, according to a user input to select a selected sensor unit from said plurality of sensor units, for sending a signal assigning the selected sensor unit;
   a control unit for monitoring the signal assigning the selected senor unit; and lamps for indicating a state of that sensor unit,
   wherein said control unit sends a command to the selected senor unit to set the selected sensor unit in a ready state and a command to each other sensor unit to cause those other sensor units each to set itself in a sleep state, and
   wherein each of said lamps blinks during a transition in to the ready state and keeps lighting after being in the ready state.

2. An image sensing system according to claim 1, wherein the at least one selection unit comprises a plurality of selection units, and wherein, according to a user input to select a selected sensor unit from said plurality of sensor units, each of said plurality of selection units can send a signal assigning the selected sensor unit.

3. An image sensing system according to claim 1 or 2, wherein the sleep state is a low current state in which a current supplied to a sensor unit is low.

4. An image sensing system according to claims 1 and 2, wherein the sleep state is a low current state in which a current supplied to a sensor unit is cut off.

* * * * *

UNITED STATES PATENT AND TRADEMARK OFFICE
CERTIFICATE OF CORRECTION

PATENT NO. : 6,977,990 B2  Page 1 of 1
APPLICATION NO. : 10/642232
DATED : December 20, 2005
INVENTOR(S) : Junichi Yamayoshi It is certified that error appears in the above-identified patent and that said Letters Patent is hereby corrected as shown below:

<u>COLUMN 1</u>

Line 36, "sensed" should read --being sensed--.

<u>COLUMN 6</u>

Line 16, "in to" should read --into--.

Signed and Sealed this

Fourth Day of July, 2006

JON W. DUDAS
*Director of the United States Patent and Trademark Office*